United States Patent

Nishijima et al.

[11] Patent Number: 5,899,941
[45] Date of Patent: May 4, 1999

[54] ARTIFICIAL INTERVERTEBRAL DISK

[75] Inventors: Yuichiro Nishijima, Kanazawa; Koichi Tanaka, Nagoya, both of Japan

[73] Assignee: Chubu Bearing Kabushiki Kaisha, Aichi-ken, Japan

[21] Appl. No.: 08/987,510

[22] Filed: Dec. 9, 1997

[51] Int. Cl.[6] .................................. A61F 2/44; A61F 2/30
[52] U.S. Cl. ............................................... 623/17; 623/18
[58] Field of Search ................................ 623/17; 606/61; 403/122

[56] References Cited

U.S. PATENT DOCUMENTS

| | | | |
|---|---|---|---|
| 5,425,773 | 6/1995 | Boyd et al. | 623/17 |
| 5,544,968 | 8/1996 | Goellner | 403/122 |
| 5,676,701 | 10/1997 | Yuan et al. | 623/17 |

FOREIGN PATENT DOCUMENTS

| | | | |
|---|---|---|---|
| 91/13598 | 9/1991 | WIPO | 623/17 |
| 93/10725 | 6/1993 | WIPO | 623/17 |

*Primary Examiner*—Mickey Yu
*Assistant Examiner*—Alvin Stewart
*Attorney, Agent, or Firm*—Flynn, Thiel, Boutell & Tanis, P.C.

[57] ABSTRACT

An operation for fixing a vertebral column by an autogenetic or a spacer has no movability or motion property, leading to an impedance of everyday life functions and recurrence of damage at the treated part. An artificial intervertebral disk comprising a movable protrusion which is formed integrally with a base body of a first connecting body and which has an arc shape in cross section at the tip end thereof, a movable receiver part formed by depressing a base body of a second connecting body at an opposing inner surface thereof, and wherein the movable receiver part comprises a receiving surface which contacts the tip end of the movable protrusion and a bank protruding from the periphery of the receiving surface, and a vertical gap is defined between the first and second connecting bodies and a horizontal gap is defined between the outer periphery of the movable protrusion and the inner periphery of the bank, whereby the first and second connecting bodies of the artificial intervertebral disk mounted on the ailed part have movability such as turning and sliding to thereby give a motion property to the vertebral column so that the aforementioned problem is solved.

10 Claims, 10 Drawing Sheets

FIG. I (A)
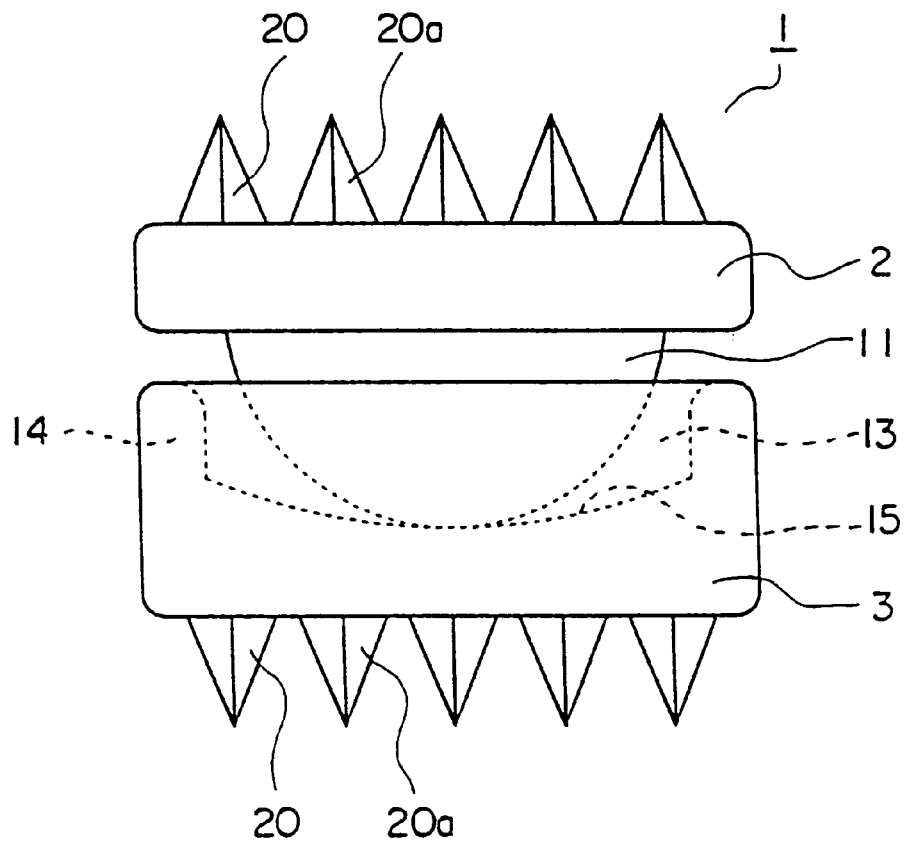
FIG. I (B)
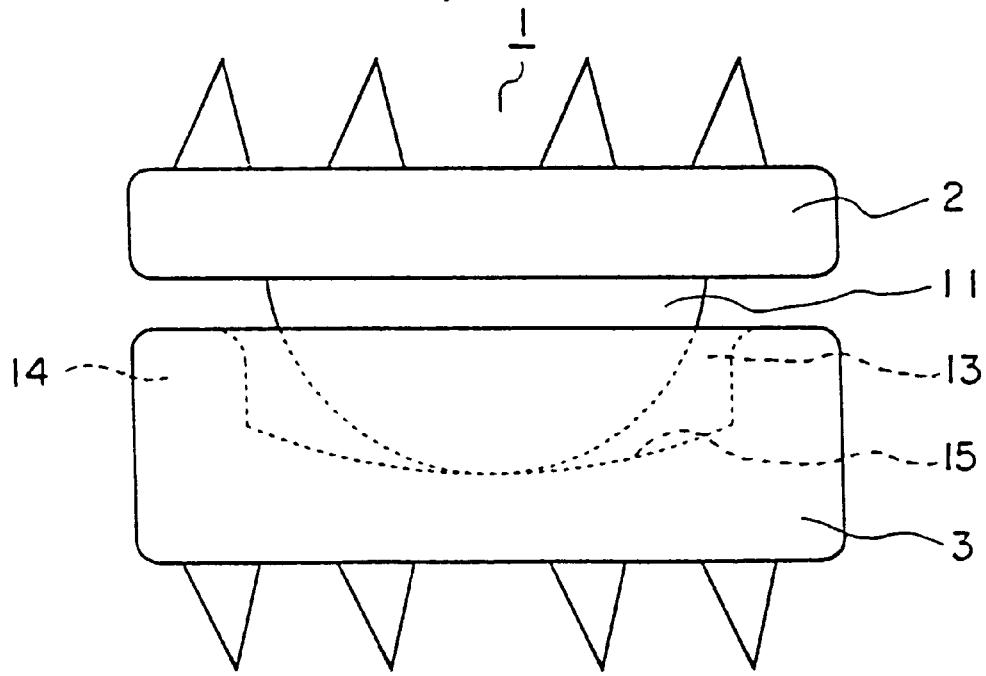

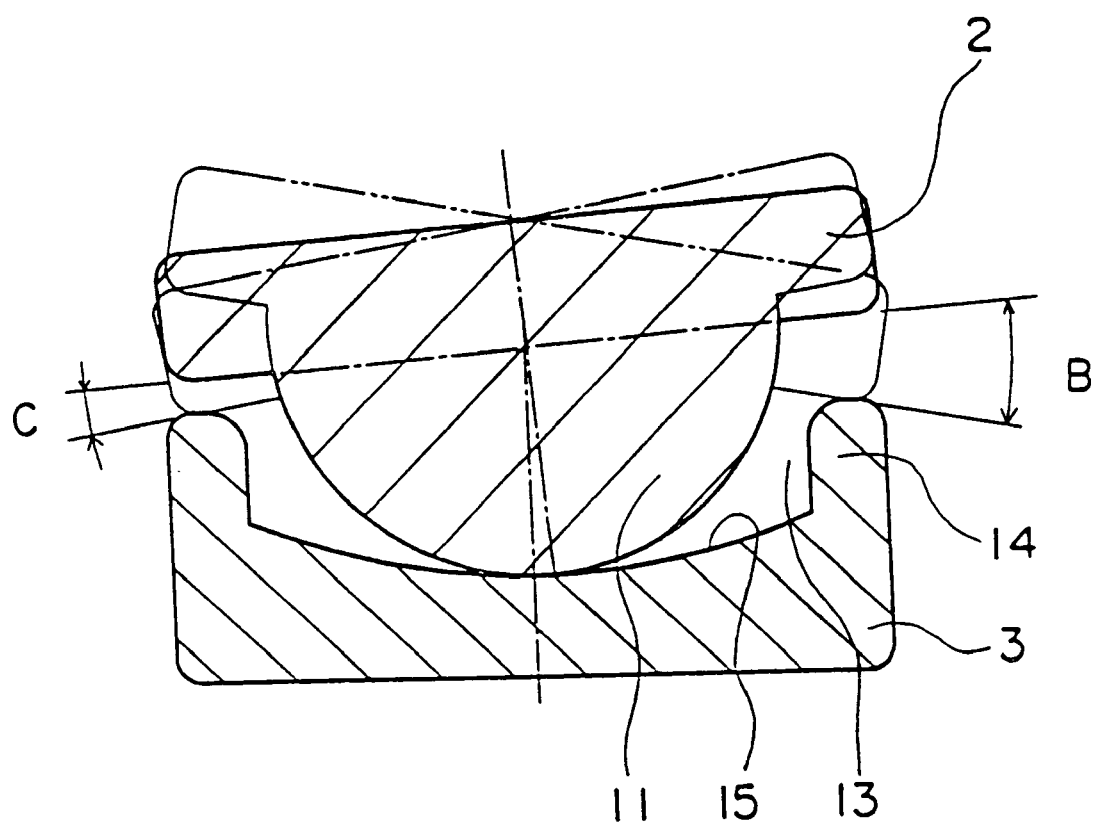

ARTIFICIAL INTERVERTEBRAL DISK

BACKGROUND OF THE INVENTION

1. Field of the invention

The present invention relates to an artificial intervertebral disk for use in treatment of a hernia of an intervertebral disk, other diseases or ailed parts, and damages of a vertebral column such as cervical vertebral and lumbar vertebra which is caused by an accident, etc. wherein the artificial intervertebral disk is inserted into the cut ailed part after cutting the damaged intervertebral disk for connecting normal vertebral bodies which adjoin vertically.

2. Prior Art

The vertebral bodies of the vertebral column which range vertically are connected with one another by intervertebral disks, and the motion of the vertebral column is supported by the intervertebral disks.

The hernia of an intervertebral disk, other disease and damages, etc. develop owing to unnatural exercise or motion, aging, denature etc., and the intervertebral disk is cut, and a surgical operation for inserting an autogenetic or an artificial intervertebral disk into the ailed part has been carried out.

In the operation for fixing the vertebral column between the artificial intervertebral disk 1 which is formed substantially in a disk shape or a rectangular parallelepiped shape serving as an autogenetic or a spacer, such autogenetic merely functions to support a load but does not function to support the motion of the vertebral column.

Accordingly, the artificial intervertebral disk does not follow the motion of a human body, which impedes the everyday life and an excessive external force is applied thereto, thereby forcibly apply an excessive burden in an everyday life of a treated part between the upper and lower intervertebral disks of a treated part, leading to a problem that the medically treated part or the upper and lower peripheries thereof are liable to be damaged again.

SUMMARY OF THE INVENTION

It is an object of the invention to provide an artificial intervertebral disk (hereinafter referred to simply as an artificial intervertebral disk 1) to which a motion is given properly and which is inserted and implanted between the vertebral bodies which adjoin vertically.

The problem of the conventional technique is that the vertebral column fixing operation uses an autogenetic or a spacer having no movability or motion property, which impedes everyday life functions and damage at the treated part is liable recur. The present invention is to provide an artificial intervertebral disk comprising a movable protrusion 11 which is formed integrally with a base body of a first connecting body 12 and which has an arc shape in cross section at the tip end thereof, a movable receiver part 3 formed by depressing a base body 12 of a second connecting body 3 at an opposing inner surface thereof. The movable receiver part 13 comprises a receiving surface 15 which contacts the tip end of the movable protrusion 11 and a bank 14 protruding from the periphery of the receiving surface 15, and a vertical gap T1 is defined between the first and second connecting bodies 2 and 3 and a horizontal gap T2 is defined between the outer periphery of the movable protrusion 11 and the inner periphery of the bank 14. The first and second connecting bodies 2 and 3 of the artificial intervertebral disk 1 mounted on the ailed part have movability such as turning and sliding to thereby give a motion property to the vertebral column so that the aforementioned problem is solved.

BRIEF DESCRIPTION OF DRAWINGS

FIG. 1(A) is a side view of an artificial intervertebral disk and FIG. 1(B) is a front view of the artificial intervertebral disk according to a first embodiment of the present invention;

FIG. 5 is a sectional end view of a main part of the artificial intervertebral disk in FIG. 4 showing a state where the upper and lower first and second connecting bodies turn and slide at the contacting surface whereby the first and second connecting bodies 2 and 3 are inclined and displaced;

DESCRIPTION OF THE PREFERRED EMBODIMENT

An artificial intervertebral disk 1 according to a first embodiment of the invention will be now described with reference to FIGS. 1 to 6.

The artificial intervertebral disk 1 comprises, as show in FIGS. 1(A) and 1(B), a pair of upper and lower first and second connecting bodies 2 and 3.

Figure 2:
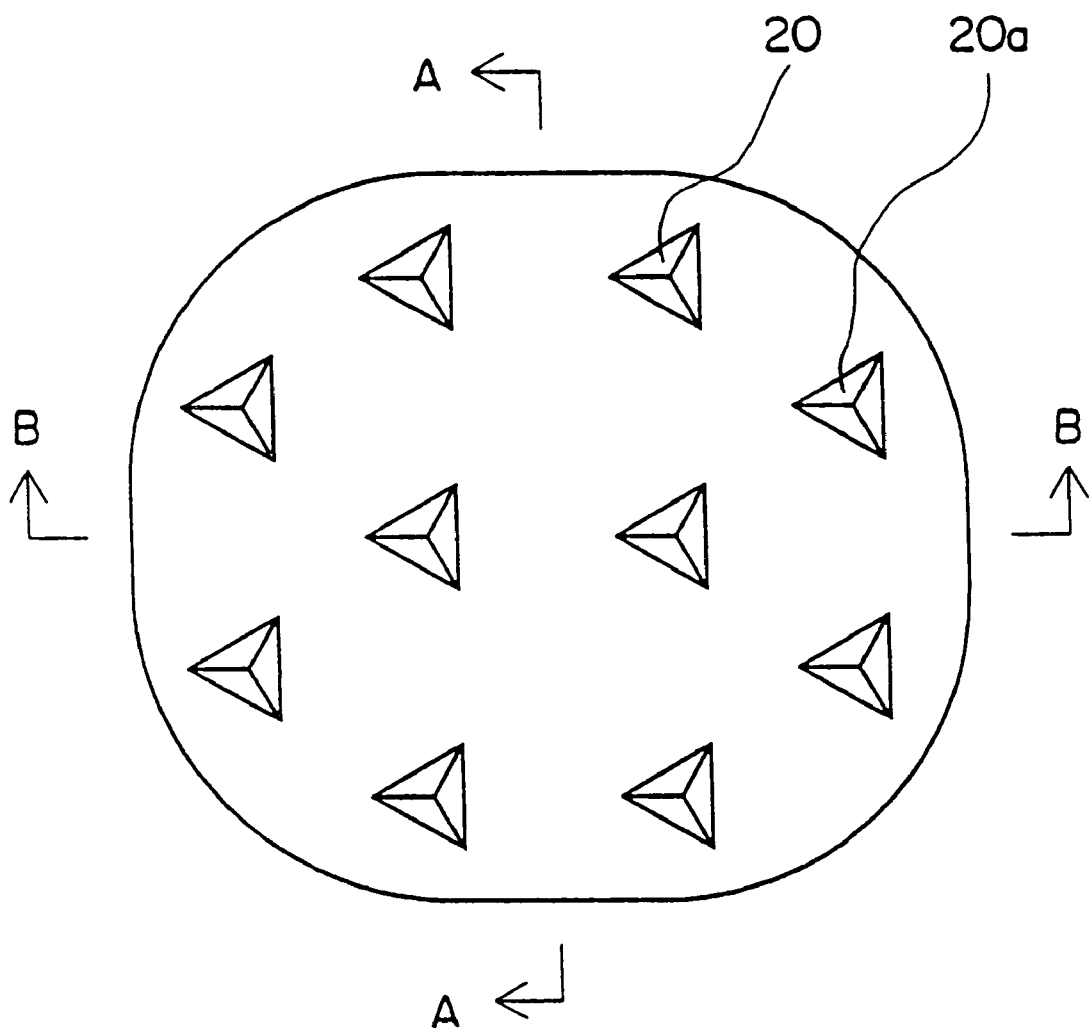
FIG. 2 is a plan view of FIG. 1(A)
Figure 3A:
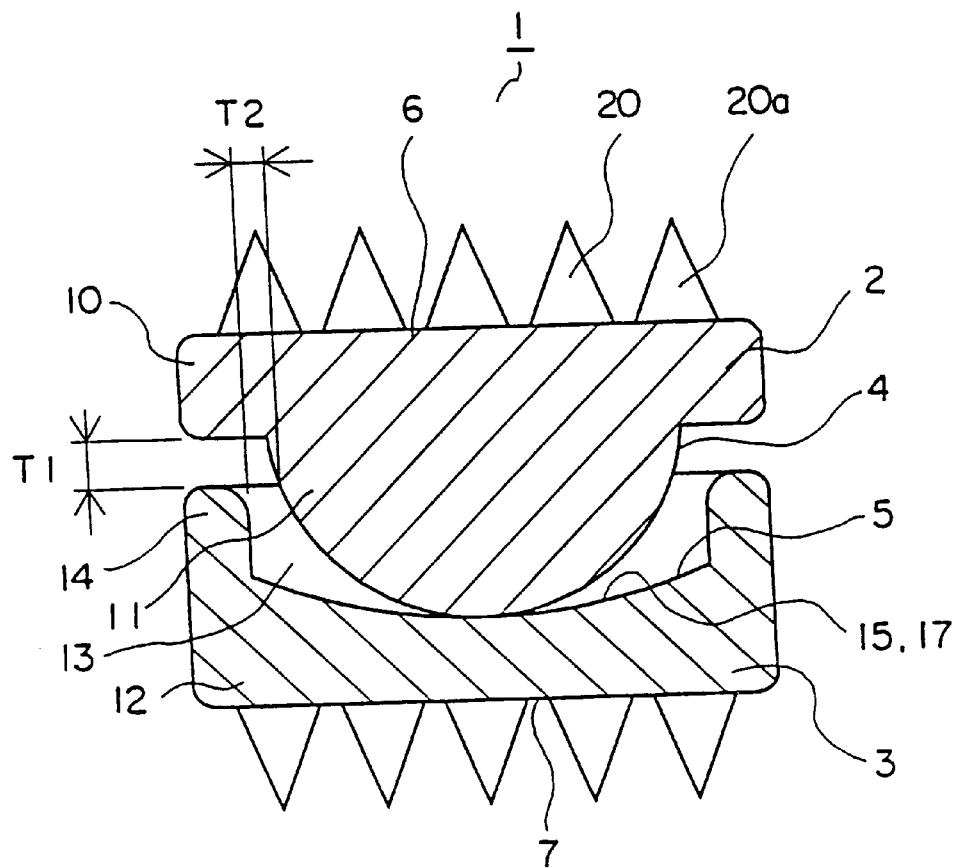
FIG. 3(A) is a sectional view of FIG. 2 taken along line A—A and FIG. 3(B) is a sectional view of FIG. 2 taken along line B—B.
Figure 3B:
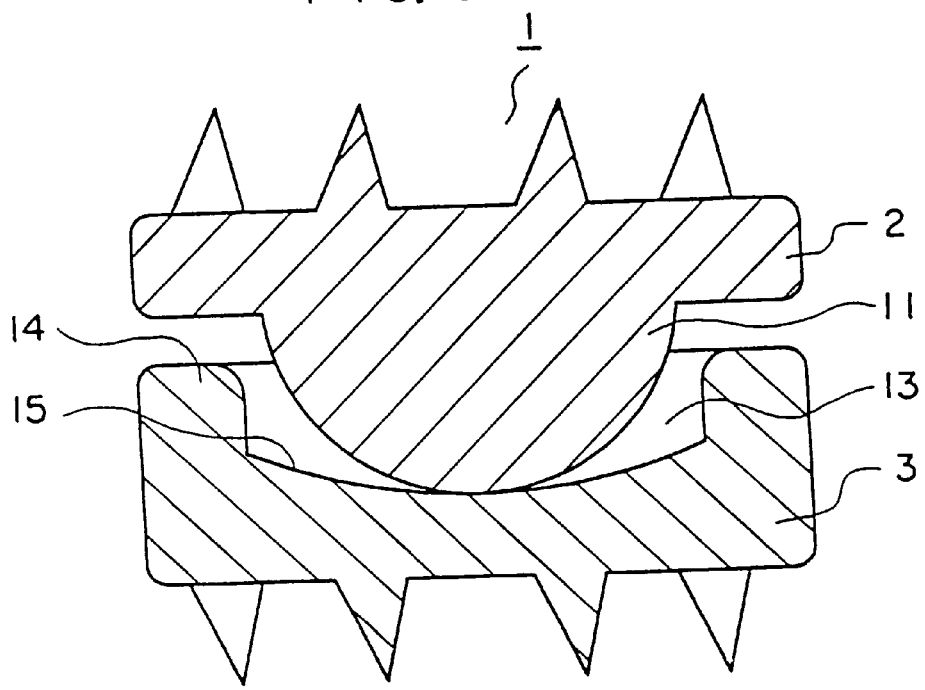
Figure 4:
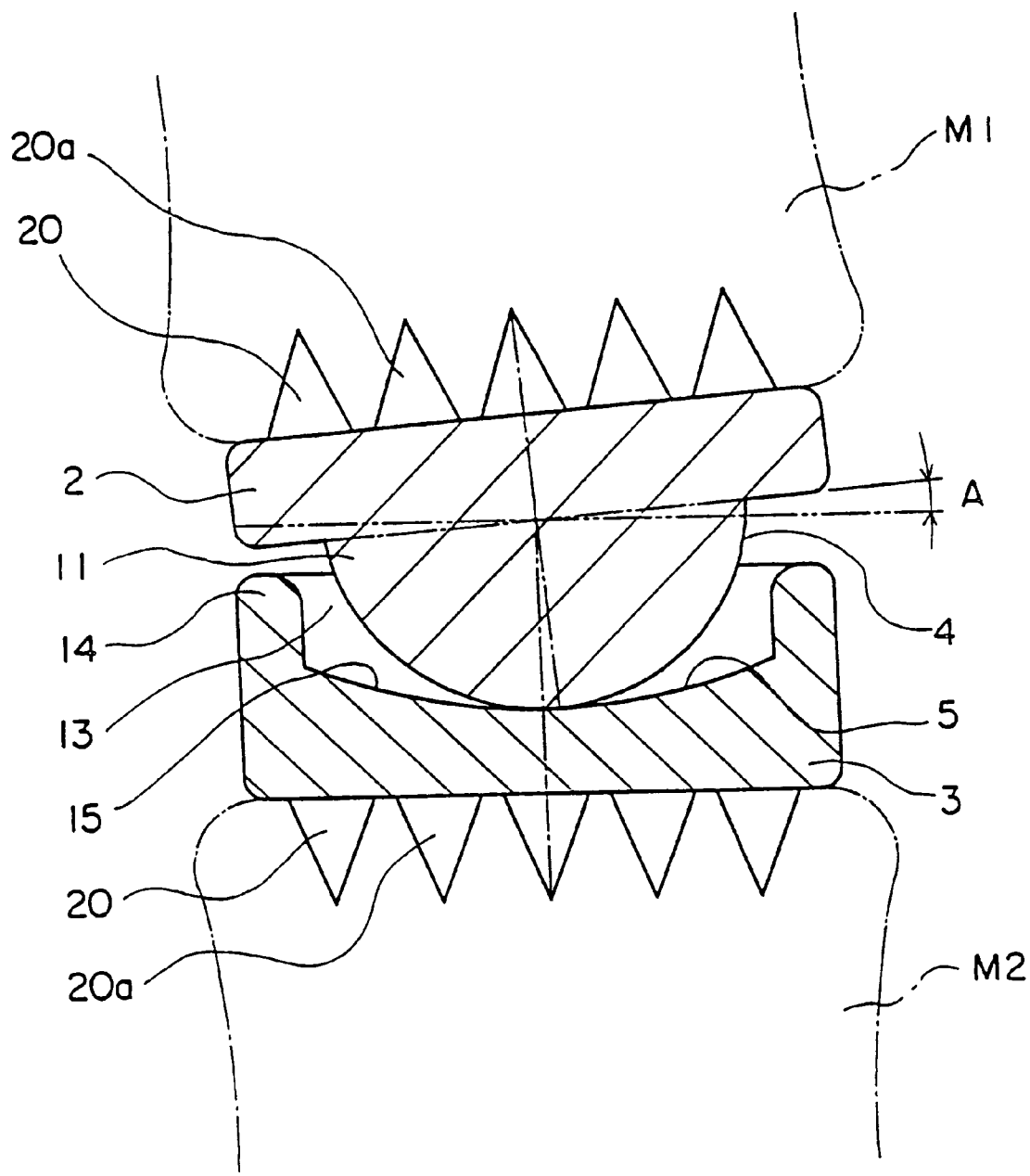
FIG. 4 is a sectional view showing a main part of the artificial intervertebral disk which is inserted into an ailed part.

As shown in FIG. 4, when the artificial intervertebral disk 1 is mounted on an ailed part, the opposing inner surfaces 4 and 5 of the first and second connecting bodies 2 and 3 are connected to each other at the contacting surfaces thereof (see FIGS. 5 and 6), and upper and lower outer surfaces 6 and 7 of the first and second connecting bodies 2 and 3 are connected to upper and lower vertebral bodies M1 and M2 of the cut artificial intervertebral disk 1 in a surface contacting state.

The first connecting body 2 is positioned at the upper side and the second connecting body 3 is positioned at the lower side in the FIGS. 1 to 4, but they may be turned upside down.

As shown in FIGS. 1(A) and 1(B) and FIGS. 3(A) and 3(B), a hemispherical movable protrusion 11 having an arc shape at the tip end lower portion in cross section is formed integrally with a flat-shaped base body 10 at the lower side.

On the other hand, the second connecting body 3 has a flat shaped base body 12 which is depressed to form a movable receiver part 13, and the movable protrusion 11 of the first connecting body 2 is movably engaged with the receiving part 13 at the upper surface thereof.

More in detail, a bank 14 is formed integrally with the base body 12 at the upper peripheral side thereof to protrude therefrom, and a receiving surface 15 having an arc surface 17 which is low at the central portion thereof is formed on the inner bottom surface of the bank 14, wherein a recessed part of the upper opening formed by the bank 14 and receiving surface 15 forms the movable receiver part 13.

In the state where the movable protrusion 11 provided on the first connecting body 2 and the movable receiver part 13 provided on the second connecting body 3 are engaged and connected with each other, a vertical gap T1 having a given interval is defined between the lower surface of the base body 10 of the first connecting body 2 and the upper end of the bank 14 of the second connecting body 3, and a horizontal gap T2 having a given interval is defined between the outer periphery of the movable protrusion 11 of the first connecting body 2 and the inner periphery of the bank 14 of the second connecting body 3.

Next, as shown in FIGS. 1(A) and 1(B), FIG. 2 and FIGS. 3(A) and 3(B), a plurality of triangular pyramidal fixed protrusions 20, 20a, . . . are integrally formed on the outer surfaces 6 and 7 of the first and second connecting bodies 2 and 3.

Although the fixed protrusions 20, 20a, . . . have triangular pyramidal shapes, they may be selected arbitrarily from any shapes such as conical, square, or triangular shape in cross section, or a shape having a long ridge line, etc.

As shown in FIG. 4, the first and second connecting bodies 2 and 3 of the artificial intervertebral disk 1 which are inserted into the normal vertebral bodies M1 and M2 in a surface contacting state during the surgical operation are pressed by the upper and lower vertebral bodies M1 and M2, so that the fixed protrusions 20, 20a, . . . and the vertebral bodies M1 and M2 are firmly connected with one another as time passes after the surgical operation.

A part to be grasped or a notch or the like, not shown, may be formed on the outer portion, etc. of the artificial intervertebral disk 1 when the artificial intervertebral disk 1 is inserted into the ailed part for the surgical operation, and for the convenience of the handling of surgical jig.

The operation of the artificial intervertebral disk 1 will be now described as follows.

In the artificial intervertebral disk 1 inserted into the ailed part, the vertebral column is inclined forward physiologically like a bow as shown in FIG. 4, although it depends on the ailed part where the artificial intervertebral disk 1 is inserted into the lumber vertebra or cervical vertebral so that the first connecting body 2 is inclined relative to the second connecting body 3.

The insertion inclination angle A of the upper vertebral body M1 (first connecting body 2) is about 4.5° relative to the lower vertebral body M2 (second connecting body 3) in FIG. 4.

In such an inserting state, various motion modes occur depending on the change of the posture of the human body in everyday life, so that the first connecting body 2 is inclined and displaced relative to the second connecting body 3.

For example, as shown in FIG. 5, the contacting surface of the movable protrusion 11 of the first connecting body 2 relative to the receiving surface 15 of the second connecting body 3 slides back and forth so that the second connecting body 3 is turnable.

Figure 6A:
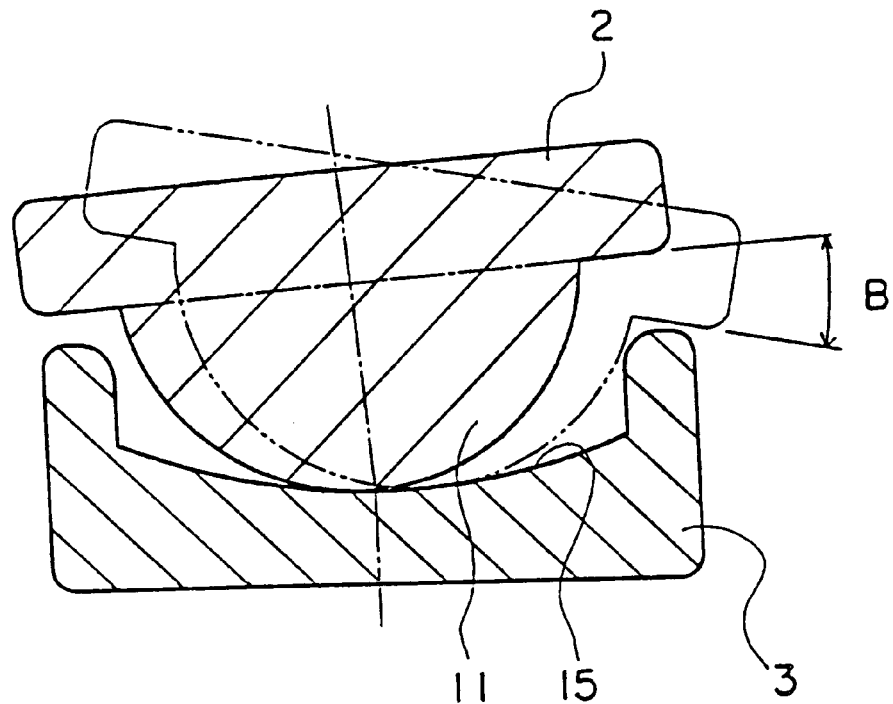
FIGS. 6(A) and 6(B) are sectional views is a sectional end view of the main part of the artificial intervertebral disk in FIG. 4 showing a state where the contacting surfaces move and turn at the state where the first and second connecting bodies 2 and 3 contact each other and wherein the first and second connecting bodies 2 and 3 are inclined and displaced.
Figure 6B:
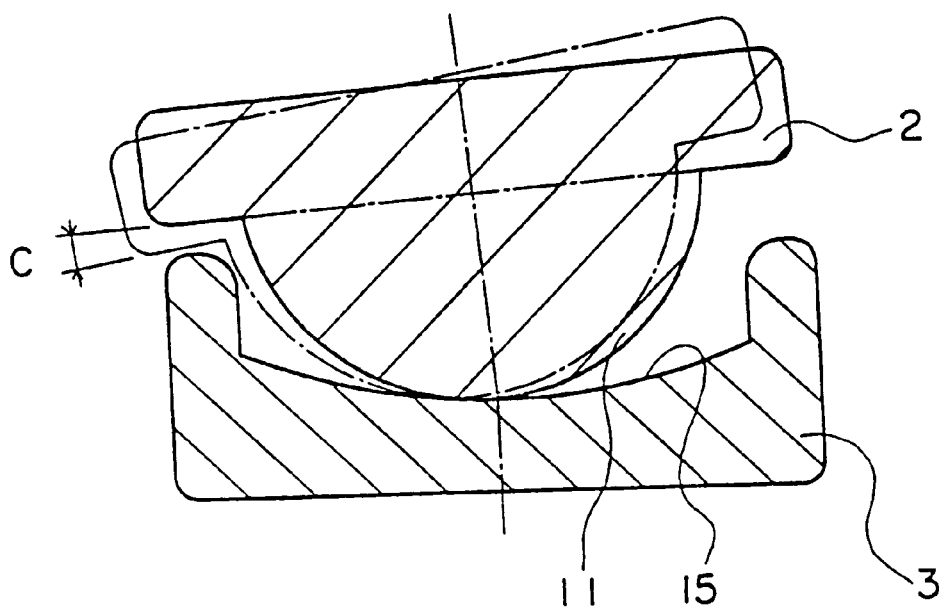

Alternately, as shown in FIGS. 6(A) and 6(B), the movable protrusion 11 turns on the receiving surface 15 of the second connecting body 3 so that the horizontal position of the second connecting body 3 relative to the first connecting body 2 moves.

As a motion mode of the artificial intervertebral disk 1, two examples are explained but these two examples may occur at the same time, and hence the artificial intervertebral disk 1 has the movability or motion property considering the above.

Although the inclination angles of the first and second connecting bodies 2 and 3 are determined at the time of the insertion of the artificial intervertebral disk 1 and the motion thereof, the vertical gap T1 and horizontal gap T2 between the artificial intervertebral disk 1 and the first connecting body 2 expand or contract owing to the change, i.e. the increase or decrease of the inclination angles depending on the inserting state of the artificial intervertebral disk 1 into the ailed part.

In the case of the artificial intervertebral disk 1 shown in FIG. 5 and FIGS. 6(A) and 6(B), it is preferable to set the intervals of the vertical gap T1 and horizontal gap T2 so that the forward inclination angle B when the vertebral column flexes forward may be about 14 to 15° and the backward inclination angle C when it flexes backward may be about 6 to 8°.

Although the forward and backward inclination angles B and C when the vertebral column flexes forward and backward are determined by the condition of an able-bodied, the artificial intervertebral disk 1 can be inserted into the ailed part with a given angle and the sufficient motion property is secured even if the base bodies 10 and 12 of the first and second connecting bodies 2 and 3 may be set to be in parallel with each other when manufacturing the first and second connecting bodies 2 and 3.

The widths of the vertical gap T1 and horizontal gap T2 may be determined to secure the inserting condition of the artificial intervertebral disk and the motion property of the artificial intervertebral disk 1 after the surgical operation.

The motion property of the vertebral column when it flexes back and forth will be now described. The normal intervertebral disk is differentiated in the height at the front portion (belly side) and the back portion (back side), that is, since the intervertebral disk at the front portion is slightly higher than that at the back portion so that the lumber vertebra and cervical vertebral have curved portions at the front portion so that they flex forward (lean backward) physiologically.

The motion of the lumber vertebra, etc. is not a simple three-dimensional movement about a specific point but includes a slight horizontal movement in the back and forth directions.

The first embodiment has the motion mode similar to such a complex motion mode.

The second to fifth embodiments which are modified examples of the first embodiment of the invention will be now described as follows.

Figure 7A:
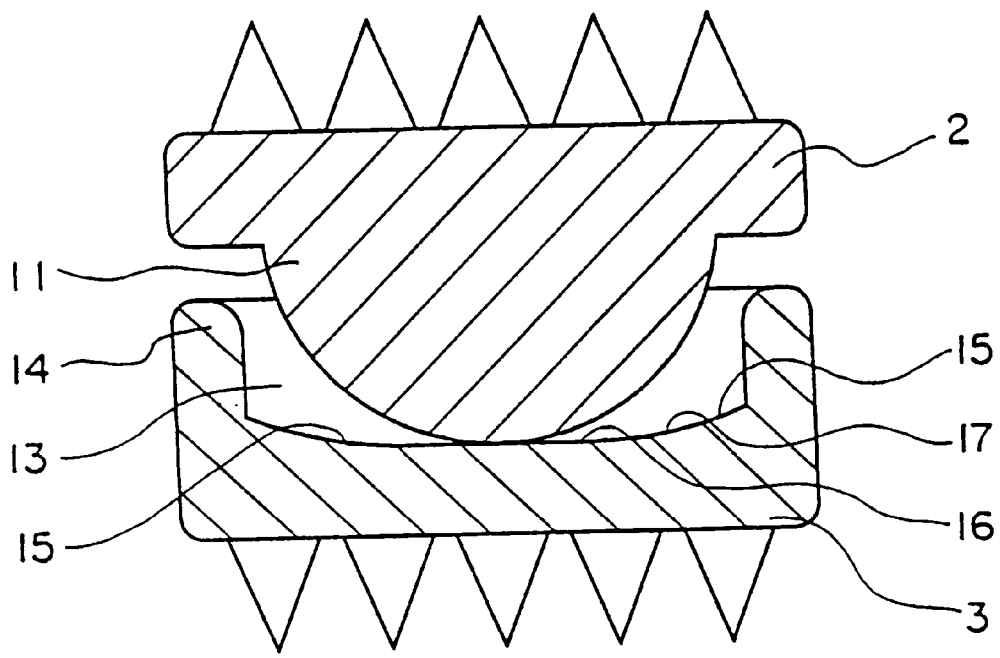
FIG. 7(A) and FIG. 7(B) are sectional views of an artificial intervertebral disk according to a second embodiment of the invention in which the central portion of the receiving surface 15 has a horizontal surface.
Figure 7B:
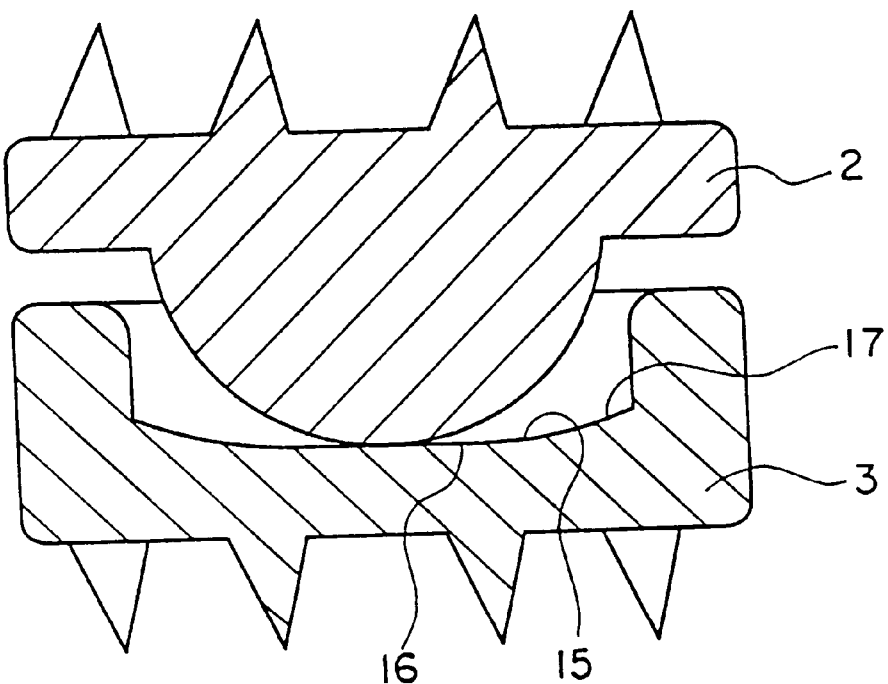

In the artificial intervertebral disk 1 of the second embodiment shown in FIGS. 7(A) and 7(B), the receiving surface 15 is formed of a horizontal surface 16 which is low at the central portion and an arc surface 17 which is high at the periphery thereof compared with the receiving surface 15 of the first embodiment having the arc surface 17 which is low at the central portion.

Figure 8A:
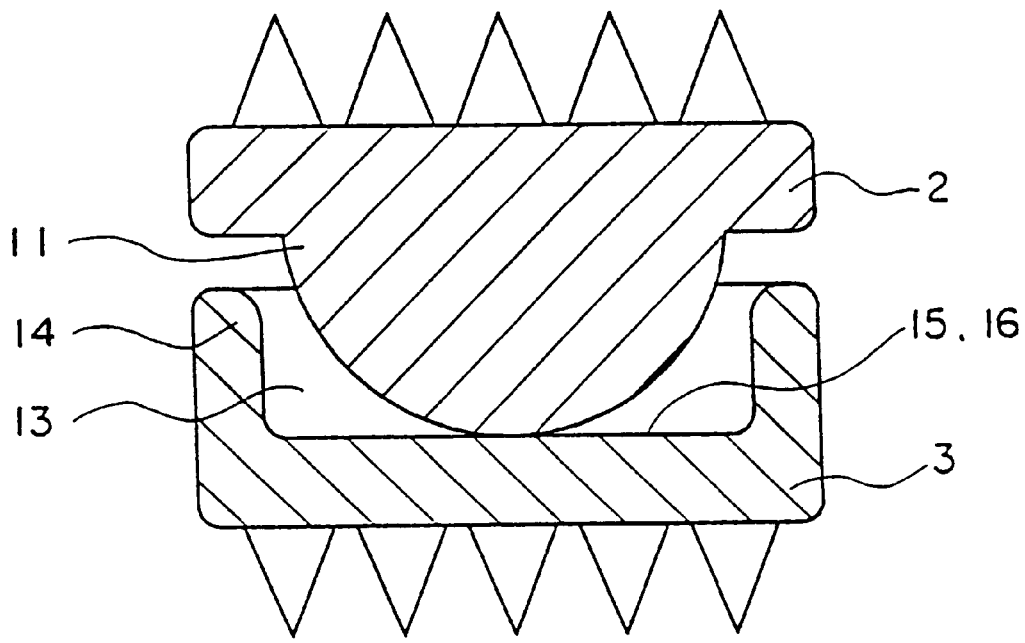
FIG. 8(A) and FIG. 8(B) are sectional views of an artificial intervertebral disk according to a third embodiment of the invention in which the entire receiving surface is formed of a horizontal surface.
Figure 8B:
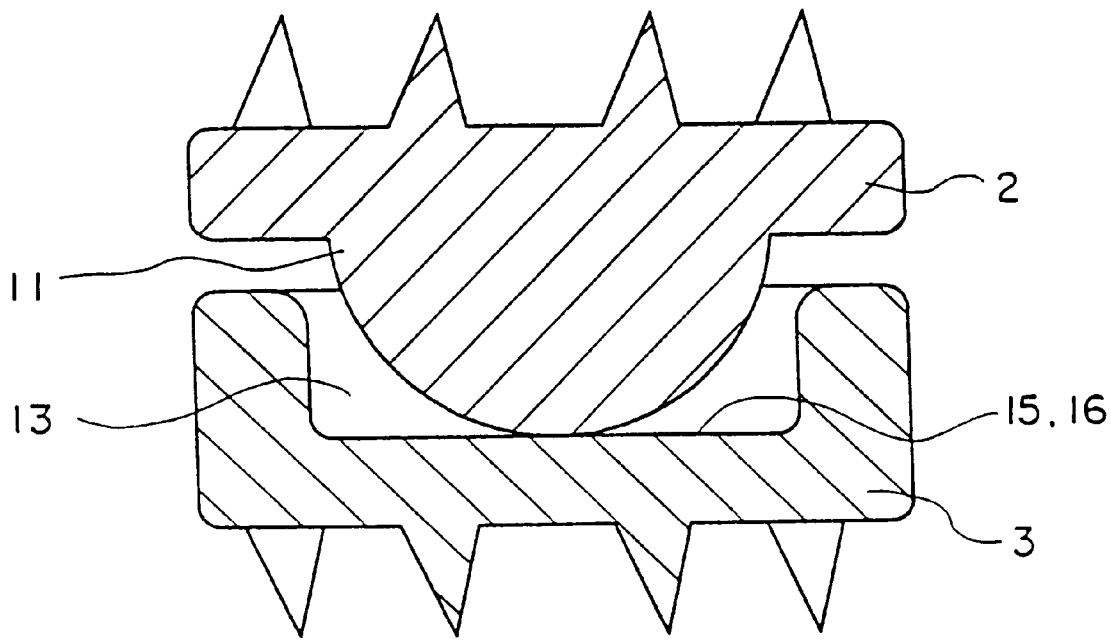

In the artificial intervertebral disk 1 of the third embodiment shown in FIGS. 8(A) and 8(B), the receiving surface 15 is formed of the horizontal surface 16.

Figure 9A:
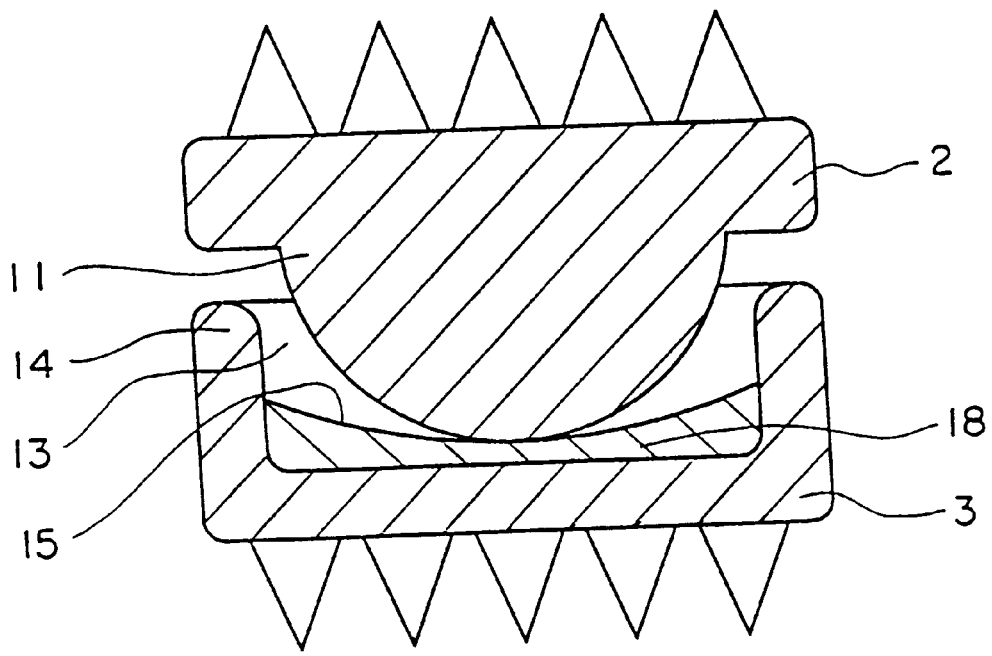
FIG. 9(A) and FIG. 9(B) are sectional views of an artificial intervertebral disk according to a fourth embodiment of the invention in which the receiving surface has an inner surface layer made of different materials.
Figure 9B:
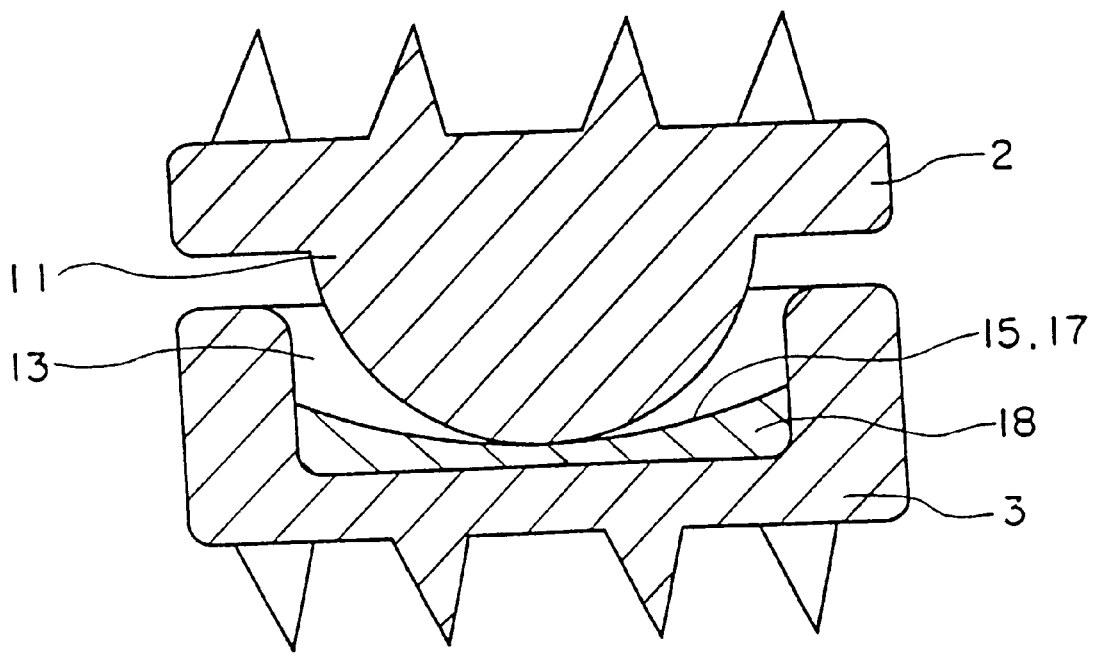
Figure 10A:
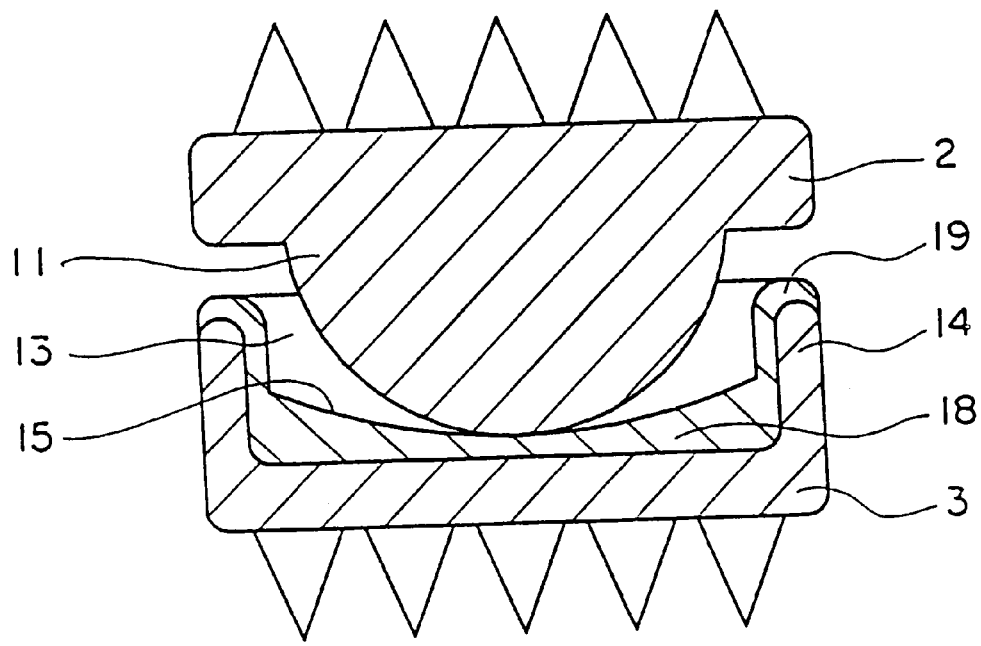
FIG. 10(A) and FIG. 10(B) are sectional views of an artificial intervertebral disk according to a fifth embodiment of the invention in which a movable receiver part including the receiving surface has an inner surface layer made of different materials.
Figure 10B:
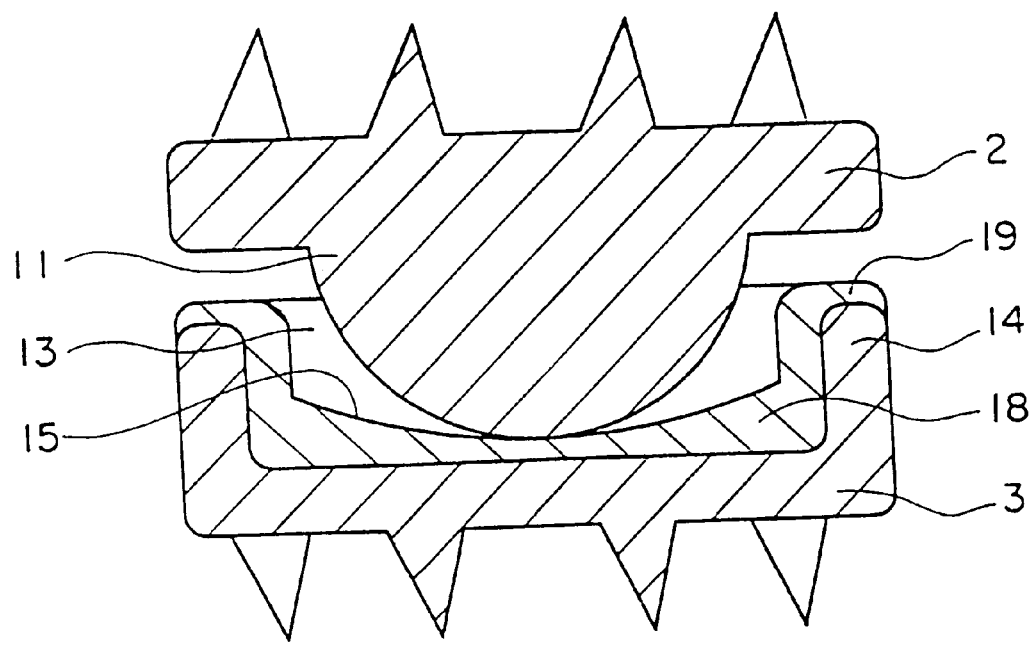

In the artificial intervertebral disk 1 of the forth and fifth embodiments shown in FIGS. 9(A) and 9(B), and FIGS. 10(A) and 10(B), the material of an inner surface layer 18 of the movable receiver part 13 is different from that of the movable receiver part 13, wherein the material of the inner surface layer 18 of the receiving surface 15 alone is different in FIGS. 9(A) and 9(B) while the materials of the inner surface layer 18 of the bank 14 and a top end layer 19 as well as the receiving surface 15 are different in FIGS. 10(A) and 10(B).

Although the shapes shown in FIGS. 9(A) and 9(B) and FIGS. 10(A) and 10(B) correspond to those of the first embodiment, they may apply to those of the second and third embodiments.

The materials of the first and second connecting bodies 2 and 3 in the first, second and third embodiments, and the materials of the first and second connecting bodies 2 and 3 and those of the inner surface layer 18 and the top end layer 19 in the fourth and fifth embodiments are respectively formed of a material having stability inside the living body such as adaptability for a human body (affinity), mechanical strength, and corrosion resistance.

For example, the material of the first and second connecting bodies 2 and 3 comprises stainless steel, titanium, tantalum, platinum, and alloys thereof and it is worked in a given size and shape, and particularly, the outer surfaces 6 and 7, the fixed protrusions 20, 20a, . . . which are connected with the vertebral bodies M1 and M2 are coated with hydroxyapatite or other affinity material having excellent affinity with a living body.

The first and second connecting bodies 2 and 3 may be formed of aluminum, zirconia and a ceramic material such as appetite instead of a metallic material, and these materials may be appropriately changed and replaced by those having affinity with a living body and those which are subjected to a surface treatment.

Further, employed as a material for the inner surface layer 18 and the top end layer 19 is that having excellency in wear which is caused by contact and friction between the first and second connecting bodies 2 and 3 when they move, for example, high polymer resin such as polyethylene or the like which has such hardness that the material is not compressed and deformed when the artificial intervertebral disk 1 is inserted into the human body.

In other words, since the artificial intervertebral disk 1 comprises a pair of upper and lower first connecting bodies 2 and 3, the artificial intervertebral disk 1 is composed of two pieces, and the artificial intervertebral disk 1 can be simply manufactured. Accordingly, it is possible to easily set the first and second connecting bodies 2 and 3 serving as two pieces of the artificial intervertebral disk 1.

Further, since the movable protrusion 11 is formed integrally with the base body 10 of the first connecting body 2 at the opposing inner surface 4 wherein the movable protrusion 11 has the arc shape at the tip end thereof in cross section, while the movable receiver part 13 is formed by depressing the base body 12 of the second connecting body 3 at the opposing inner surface 5, so that the movable protrusion 11 of the first connecting body 2 has movability, namely, the movable protrusion 11 is turned and slidably moved on the receiving surface 15 of the second connecting body 3. As a result, motion property is given to the vertebral column on which the artificial intervertebral disk 1 is mounted so that the function of the human body at the normal time is recovered so that the everyday life is not impeded, and no unnatural force is applied between the normal vertebral bodies and the intervertebral disks, thereby preventing the recurrence of the treated part.

Still further, since the movable receiver part 13 comprises the receiving surface 15 which contacts the tip end of the movable protrusion 11 and the bank 14 protruding from the periphery of the receiving surface 15, the movable protrusion 11 is changed in position and posture thereof inside the movable receiver part 13 so that the movable protrusion 11 is not removed from the movable receiver part 13, namely, the first connecting body 2 is not separated from the second connecting body 3, thereby improving the stability.

Still further, since the vertical gap T1 is defined between the opposing inner surface 4 of the base body 10 of the first connecting body 2 and the top end of the base body 10, and the horizontal gap T2 is defined between the outer periphery of the movable protrusion 11 and the inner periphery of the bank 14, the amount of motion is secured by appropriately setting the vertical gap T1 and horizontal gap T2. As a result, the excessive motion of the movable protrusion 11 on the receiving surface 15 in all directions can be restricted by the bank 14, etc., thereby securing the safety.

Still more further, since the receiving surface 15 is formed of the arc surface 17 which is low at the central portion, or the central portion of the receiving surface 15 has the horizontal surface 16, and the horizontal surface 16 is formed of the arc surface 17 at the periphery thereof which is high at the outer side thereof, the movable protrusion 11 is liable to move on the central portion of the receiving surface 15, and it is possible to easily align the center of the vertebral column, and the receiving surface 15 is formed of the horizontal surface 16 so that the movable protrusion 11 can perform the motion including the back and forth movements.

More still further, the inner surface layer 18 of the receiving surface 15 in the movable receiver part 13 or the inner surface layer 18 of the bank 14 and the top end layer 19 are respectively made of a material having low wear, the receiving surface 15 is hardly worn even by the motion between the movable protrusion 11 and receiving surface 15, thereby maintaining the life and function of the artificial intervertebral disk 1 or the shock caused by the contact of the bank 14 against the top end layer 19 can be absorbed.

Since the first connecting body 2 is inclined relative to the second connecting body 3 when the artificial intervertebral disk 1 is mounted on an 5 ailed part, and the first connecting body 2 can be inclined relative to the second connecting body 3 by 14° to 15° forward and 6° to 8° backward when it is in a state of movement, it is possible to carry out the motion like at the normal condition, thereby giving a natural motion to the artificial intervertebral disk 1.

Since a plurality of fixed protrusions 20, 20a . . . are provided at the outer surfaces 6 and 7 of the two connecting bodies 2 and 3, it is possible to fix the artificial intervertebral disk 1 between the vertebral bodies M1 and M2, thereby achieving a very excellent practical effect.

What is claimed is:

1. An artificial intervertebral disk comprising first and second connecting bodies, wherein:

said first connecting body has a base body which is formed integrally with a movable protrusion at an opposing inner surface, wherein the movable protrusion has an arc shape in cross section at a tip end thereof, the second connecting body has a base body which is depressed to form a movable receiver part at an opposing inner surface thereof, and wherein the movable receiver part comprises a receiving surface which contacts the tip end of the movable protrusion and a bank protruding from the periphery of the receiving surface, wherein the central portion of the receiving surface has a horizontal surface, and the horizontal surface extends to an arc surface at the periphery thereof which is high at an outer side thereof; and a vertical gap is defined between the opposing inner surface of the base body of the first connecting body and a top end of the bank, and a horizontal gap is defined between an outer periphery of the movable protrusion and an inner periphery of the bank.

2. The artificial intervertebral disk according to claim 1, wherein the receiving surface of the movable receiver part has an inner surface layer made of a material having low wear.

3. The artificial intervertebral disk according to claim 1, wherein inner surface layers of the bank and the receiving surface of the movable receiver part, and a top end layer of the bank are respectively made of a material having low wear.

4. The artificial intervertebral disk according to claim 1, wherein the first connecting body is inclined relative to the second connecting body when the artificial intervertebral disk is mounted on an ailed part, and the first connecting body can be inclined relative to the second connecting body by 14° to 15° forward and 6° to 8° backward.

5. The artificial intervertebral disk according to claim 1, wherein a plurality of fixed protrusions are provided at an outer surface of the base body of the first connecting body and at an outer surface of the base body of the second connecting body, said fixed protrusions adapted to secure the first and second connecting bodies of the artificial intervertebral disk to vertebral bodies.

6. An artificial intervertebral disk comprising first and second connecting bodies, wherein:

said first connecting body has a base body which is formed integrally with a movable protrusion at an opposing inner surface, wherein the movable protrusion has an arc shape in cross section at a tip end thereof, the second connecting body has a base body which is depressed to form a movable receiver part at an opposing inner surface thereof, and wherein the movable receiver part comprises a receiving surface which contacts the tip end of the movable protrusion and a bank protruding from the periphery of the receiving surface, wherein the receiving surface is formed of a horizontal surface; and a vertical gap is defined between the opposing inner surface of the base body of the first connecting body and a top end of the bank, and a horizontal gap is defined between an outer periphery of the movable protrusion and an inner periphery of the bank.

7. The artificial intervertebral disk according to claim 6, wherein the receiving surface of the movable receiver part has an inner surface layer made of a material having low wear.

8. The artificial intervertebral disk according to claim 6, wherein inner surface layers of the bank the receiving surface of the movable receiver part, and a top end layer of the bank are respectively made of a material having low wear.

9. The artificial intervertebral disk according to claim 6, wherein the first connecting body is inclined relative to the second connecting body when the artificial intervertebral disk is mounted on an ailed part, and the first connecting body can be inclined relative to the second connecting body by 14° to 15° forward and 6° to 8° backward.

10. The artificial intervertebral disk according to claim 6, wherein a plurality of fixed protrusions are provided at an outer surface of the base body of the first connecting body and at an outer surface of the base body of the second connecting body, said fixed protrusions adapted to secure the first and second connecting bodies of the artificial intervertebral disk to vertebral bodies.

* * * * *